(12) United States Patent
Wood et al.

(10) Patent No.: US 9,586,922 B2
(45) Date of Patent: Mar. 7, 2017

(54) METHODS FOR PURIFYING 5-(HALOMETHYL)FURFURAL

(71) Applicant: MICROMIDAS, INC., West Sacramento, CA (US)

(72) Inventors: Alex B. Wood, Sacramento, CA (US); Shawn M. Browning, Sacramento, CA (US); Makoto N. Masuno, Elk Grove, CA (US); Ryan L. Smith, Sacramento, CA (US); John Bissell, II, Sacramento, CA (US)

(73) Assignee: MICROMIDAS, INC., West Sacramento, CA (US)

( * ) Notice: Subject to any disclaimer, the term of this patent is extended or adjusted under 35 U.S.C. 154(b) by 0 days.

(21) Appl. No.: 14/852,306

(22) Filed: Sep. 11, 2015

(65) Prior Publication Data
US 2016/0002191 A1    Jan. 7, 2016

Related U.S. Application Data

(63) Continuation of application No. PCT/US2014/024949, filed on Mar. 12, 2014.

(60) Provisional application No. 61/785,760, filed on Mar. 14, 2013.

(51) Int. Cl.
*C07D 307/48* (2006.01)
*C07D 307/46* (2006.01)

(52) U.S. Cl.
CPC ......... *C07D 307/46* (2013.01); *C07D 307/48* (2013.01)

(58) Field of Classification Search
CPC .................................................. C07D 307/48
See application file for complete search history.

(56) References Cited

U.S. PATENT DOCUMENTS

| | | | |
|---|---|---|---|
| 2,494,325 A | 1/1950 | Anne et al. | |
| 2,611,740 A | 9/1952 | Berriman et al. | |
| 4,001,283 A | 1/1977 | Wells, Jr. | |
| 4,424,390 A | 1/1984 | Hamada et al. | |
| 4,433,155 A | 2/1984 | Gilpin | |
| 4,971,657 A | 11/1990 | Avignon et al. | |
| 6,162,350 A | 12/2000 | Soled et al. | |
| 6,788,280 B2 | 9/2004 | Ham | |
| 7,173,142 B2 | 2/2007 | Steiner et al. | |
| 7,829,732 B2 | 11/2010 | Mascal | |
| 9,102,644 B2 | 8/2015 | Mikochik et al. | |
| 9,126,964 B2 | 9/2015 | Masuno et al. | |
| 9,388,150 B2 * | 7/2016 | Kim ..................... C07D 307/48 |
| 9,388,151 B2 | 7/2016 | Browning et al. | |
| 2007/0161795 A1 | 7/2007 | Cvak et al. | |
| 2009/0234142 A1 | 9/2009 | Mascal | |
| 2010/0083565 A1 | 4/2010 | Gruter | |
| 2010/0210745 A1 | 8/2010 | McDaniel et al. | |
| 2011/0144359 A1 | 6/2011 | Heide et al. | |
| 2014/0100378 A1 | 4/2014 | Masuno et al. | |
| 2014/0187802 A1 | 7/2014 | Mikochik et al. | |
| 2015/0203462 A1 | 7/2015 | Cahana et al. | |
| 2015/0266843 A1 | 9/2015 | Browning et al. | |
| 2016/0002190 A1 | 1/2016 | Browning et al. | |
| 2016/0168107 A1 | 6/2016 | Masuno et al. | |
| 2016/0207897 A1 | 7/2016 | Wood et al. | |

FOREIGN PATENT DOCUMENTS

| | | |
|---|---|---|
| CN | 101475544 A | 7/2009 |
| CN | 102066304 A | 5/2011 |
| CN | 102675265 A | 9/2012 |
| DE | 635783 C | 9/1936 |
| EP | 291494 A2 | 11/1988 |
| EP | 1049657 B1 | 3/2003 |
| GB | 1220851 A | 1/1971 |
| GB | 1448489 A | 9/1976 |
| RU | 2429234 C2 | 9/2011 |
| WO | 9638500 A1 | 12/1996 |
| WO | 9925675 A1 | 5/1999 |
| WO | 2009155297 A1 | 12/2009 |
| WO | 2011/161141 A1 | 12/2011 |
| WO | 2012111988 A1 | 8/2012 |
| WO | 2012170520 A1 | 12/2012 |
| WO | 2013024162 A1 | 2/2013 |
| WO | 2014066746 A1 | 5/2014 |
| WO | 2015023918 A2 | 2/2015 |

OTHER PUBLICATIONS

Aho et al., "Catalytic Pyrolysis of Biomass in a Fluidized Bed Reactor: Influence of the Acidity of H-Beta Zeolite", Trans ICheme, Part B, Process Safety and Environmental Protection, vol. 85, No. B5, Sep. 2007, pp. 473-480.

(Continued)

Primary Examiner — Golam M M Shameem
(74) Attorney, Agent, or Firm — Morrison & Foerster LLP

(57) ABSTRACT

The present disclosure provides methods for purifying a 5-(halomethyl)furfural composition, including 5-(chloromethyl)furfural, at operating conditions that decrease or minimize the decomposition or degradation of 5-(chloromethyl)furfural during the process. The methods may employ certain solvents, operating conditions, and/or techniques (e.g., gas stripping). The gaseous 5-(halomethyl)furfural produced from the process can be condensed or deposited to yield 5-(halomethyl)furfural in liquid or solid form. The solid 5-(halomethyl)furfural may be amorphous or crystalline.

8 Claims, 3 Drawing Sheets

(56) References Cited

OTHER PUBLICATIONS

Aho et al., "Catalytic Upgrading of Woody Biomass Derived Pyrolysis Vapours Over Iron Modified Zeolites in a Dual-Fluidized Bed Reactor", Fuel, vol. 89, 2010, pp. 1992-2000.
Alonso et al., "Catalytic Conversion of Biomass to Biofuels", Green Chemistry, vol. 12, No. 9, 2010, pp. 1493-1513.
Bemiller, James N., "Carbohydrates", Kirk-Othmer Encyclopedia of Chemical Technology, vol. 4, Jan. 16, 2004, pp. 696-733.
Brasholz et al., "Highly Efficient Dehydration of Carbohydrates to 5-(Chloromethyl)Furfural(CMF), 5-(Hydroxymethyl)Furfural (HMF) and Levulinic acid by Biphasic Continuous Flow Processing", Green Chemistry, vol. 13, 2011, pp. 1114-1117.
Breeden et al., "Microwave Heating for Rapid Conversion of Sugars and Polysaccharides to 5-Chloromethyl Furfural", Green Chemistry, vol. 15, 2013, pp. 72-75.
Chheda et al., "Production of 5-Hydroxymethylfurfural and Furfural by Dehydration of Biomass-Derived Mono- and Poly-Saccharides", Royal Society of Chemistry, Green Chemistry, vol. 9, 2007, pp. 342-350.
Chundury et al., "Preparation of Polymeric Building Blocks from 5-Hydroxymethyl- and 5-Chloromethylfurfuraldehyde", Industrial and Engineering Chemistry Product Research and Development, vol. 20, No. 1, 1981, pp. 158-163.
"Database WPI Week 200952", XP002684874, 4 pages.
Dunlop, A. P., "Furfural formation and Behavior", Industrial & Engineering Chemistry, vol. 40, No. 2, 1948, pp. 204-209.
Extended European Search Report (includes Supplementary European Search Report and Search Opinion) received for European Patent Application No. 14776137.3, mailed on Jul. 4, 2016, 5 pages.
Fenton et al., "LXXXV.—Derivatives of Methylfurfural", Journal of the Chemical Society, Transactions, vol. 79, 1901, pp. 807-816.
Fenton et al., "XLI.—Bromomethylfurfuraldehyde", Journal of the Chemical Society, Transactions, vol. 75, 1899, pp. 423-433.
Hamada et al., "An Improved Method for the Conversion of Saccharides into Furfural Derivative", The Chemical Society of Japan, 1982, pp. 617-618.
Haworth et al., "The Conversion of Sucrose into Furan Compounds. Part I. 5-Hydroxymethylfurfuraldehyde and Some Derivatives", Journal of the Chemical Society, 1944, pp. 667-670.
Hibbert et al., "Studies on Cellulose Chemistry II. The Action of Dry Hydrogen Bromide on Carbohydrates and Polysaccharides 1,2", Journal of the American Chemical Society, vol. 45, No. 1, 1923, pp. 176-182.
International Preliminary Report on Patentability received for PCT Patent Application No. PCT/US2012/041087, mailed on Dec. 27, 2013, 8 pages.
International Preliminary Report on Patentability received for PCT Patent Application No. PCT/US2013/066788, mailed on May 7, 2015, 9 pages.
International Preliminary Report on Patentability received for PCT Patent Application No. PCT/US2014/024940, mailed on Oct. 1, 2015, 9 pages.
International Preliminary Report on Patentability received for PCT Patent Application No. PCT/US2014/024949, mailed on Sep. 24, 2015, 15 pages.
International Preliminary Report on Patentability received for PCT Patent Application No. PCT/US2014/056572, mailed on Mar. 31, 2016, 7 pages.
International Search Report & Written Opinion received for PCT Patent Application No. PCT/US2014/056572, mailed on Nov. 24, 2014, 9 pages.
International Search Report and Written Opinion received for PCT Patent Application No. PCT/US2012/041087, mailed on Oct. 19, 2012, 12 pages.
International Search Report and Written Opinion received for PCT Patent Application No. PCT/US2013/066788, mailed on Feb. 6, 2014, 11 pages.
International Search Report and Written Opinion received for PCT Patent Application No. PCT/US2014/024940, mailed on Jul. 14, 2014, 12 pages.
International Search Report and Written Opinion received for PCT Patent Application No. PCT/US2014/024949, mailed on Jul. 11, 2014, 17 pages.
International Search Report and Written Opinion received for PCT Patent Application No. PCT/US2016/022790, mailed on Jun. 3, 2016, 8 Pages.
Jin et al., "Application of Hydrothermal Reaction to Conversion of Plant-Origin Biomasses into Acetic and Lactic Acids", Journal of Materials Science, vol. 43, No. 7, Apr. 2008, pp. 2463-2471.
Kaliyan et al., "Densification Characteristics of Corn Cobs", Fuel Processing Technology, vol. 91, No. 5, May 2010, pp. 559-565.
Kumari et al., "Synthesis of 5-Bromomethylfurfural from Cellulose as a Potential Intermediate for Biofuel", European Journal of Organic Chemistry, 2011, pp. 1266-1270.
Liley, P. E., "Section 2: Physical and Chemical Data", Perry's Chemical Rngineer's Handbook, 1997, 1 page.
Liu et al., "Theoretical Studies on Thermochemistry for Conversion of 5-Chloromethylfurfural into Valuable Chemicals", The Journal of Physical Chemistry A., vol. 115, No. 46, 2011, pp. 13628-13641.
Mascal et al., "Direct, High-Yield Conversion of Cellulose into Biofuel", Angewandte Chemie International Edition, vol. 47, 2008, pp. 7924-7926.
Mascal et al., "Dramatic Advancements in the Saccharide to 5-(Chloromethyl)furfural Conversion Reaction", Chemsuschem, vol. 2, No. 9, Sep. 21, 2009, pp. 859-861.
Mascal et al., "Towards the Efficient, Total Glycan Utilization of Biomass", Chemsuschem, vol. 2, 2009, pp. 423-426.
Moye, C. J., "5-Hydroxymethylfurfural", Reviews of Pure and Applied Chemistry, vol. 14, Jan. 1964, pp. 161-170.
Nawale et al., "Synthesis and Evaluation of Novel Thiazolidinedione Derivatives for Antibacterial Activity", Der Pharma Chemica, vol. 4, No. 6, 2012, pp. 2270-2277.
Non Final Office Action received for U.S. Appl. No. 14/124,240, mailed on Aug. 14, 2014, 13 pages.
Non Final Office Action received for U.S. Appl. No. 14/124,240, mailed on Nov. 14, 2014, 13 pages.
Non-Final Office Action received for U.S. Appl. No. 14/805,321, mailed on Aug. 11, 2016, 12 pages.
Notice of Allowance received for U.S. Appl. No. 14/438,600, mailed on Nov. 12, 2015, 6 Pages.
Notice of Allowance received for U.S. Appl. No. 14/124,240, mailed on Apr. 10, 2015, 7 pages.
Notice of Allowance received for U.S. Appl. No. 14/438,600, mailed on Mar. 14, 2016, 5 pages.
Quiroz-Florentino et al., "Total Synthesis of Naturally Occurring Furan Compounds 5-{[(4-Hydroxybenzyl)Oxy]Methyl}-2-Furaldehyde and Pichiafuran C", Synthesis, No. 7, 2011, pp. 1106-1112.
Sanda et al., "The Vilsmeier Reaction: A New Synthetic Method for 5-(Chloromethyl)-2-furaldehyde", Synthesis, No. 6, Jun. 1992, pp. 541-542.
Surh et al., "5-Sulfooxymethylfurfural as a Possible Ultimate Mutagenic and Carcinogenic Metabolite of the Maillard Reaction Product, 5-Hydroxymethylfurfural", Carcinogenesis, vol. 15, No. 10, 1994, pp. 2375-2377.
Surh et al., "Activation of the Maillard Reaction Product 5-(Hydroxymethyl)furfural to Strong Mutagens via Allylic Sulfonation and Chlorination", Chemical Research in Toxicology, vol. 7, No. 3, 1994, pp. 313-318.
Szmant et al., "The Preparation of 5-Chloromethylfurfuraldehyde from High Fructose Corn Syrup and Other Carbohydrates", Journal of Chemical Technology and Biotechnology, vol. 31, No. 1, 1981, pp. 205-212.
Timko et al., "The Furanyl Unit in Host Compounds", Journal of the American Chemical Society, vol. 96, No. 22, Oct. 30, 1974, pp. 7159-7160.
Werther, Joachim, "Fluidized-Bed Reactors", Wiley Online Library, Ullmann's Encyclopedia of Industrial Chemistry, vol. 15, 2007, 48 pages.

(56) References Cited

OTHER PUBLICATIONS

Wikipedia, "1,2-Dichloroethane", available online at <https://en.wikipedia.org/wiki/1,2-Dichloroethane> on Aug. 3, 2014, Aug. 3, 2014, 4 pages.
Worden, Edward Chauncey, "Technology of Cellulose Esters", vol. 1—Part 1, 1921, p. 186.

* cited by examiner

METHODS FOR PURIFYING 5-(HALOMETHYL)FURFURAL

CROSS-REFERENCE TO RELATED APPLICATION

This is application is a continuation application of International Application PCT/US2014/024949, with an international filing date of Mar. 12, 2014, which claims priority to and the benefit of U.S. Provisional Patent Application No. 61/785,760, filed Mar. 14, 2013, the disclosures of which are incorporated herein by reference in their entireties.

FIELD

The present disclosure relates generally to the production of furfural compounds, and more specifically to the purification of 5-(halomethyl)furfural, such as 5-(chloromethyl) furfural.

BACKGROUND

Efforts to reduce dependence on fossil fuels for transportation fuel and as feedstock for industrial chemicals have been undertaken for decades, with a particular focus on enabling economic feasibility of renewable feedstocks. Heightened efforts are being made to more effectively utilize renewable resources and develop "green" technologies, due to continued long-term increases in the price of fuel, increased environmental concerns, continued issues of geopolitical stability, and renewed concerns for the ultimate depletion of fossil fuels.

Cellulose in biomass is commonly used as a feedstock for biofuel production. For example, cellulose can be used to produce ethanol. Cellulose can also be used to produce furan-based biofuels by way of 5-(halomethyl)furfural, such as 5-(chloromethyl)furfural (CMF). CMF can be converted into 5-(ethoxymethyl)furfural, a compound considered as a promising diesel fuel additive. Alternatively, CMF can also be converted into 5-methylfurfural, another compound considered as a promising a biofuel candidate.

The production of CMF from cellulose was first described in the early 1900s. Currently, various synthetic routes are known in the art to produce CMF. CMF is typically produced as an oily residue that can be purified by distillation. See e.g., Szmant & Chundury, *J. Chem. Tech. Biotechnol.* 1981, 31, 205-212. CMF, however, is known to decompose at high temperatures. This presents a challenge for purifying CMF by distillation or for obtaining gaseous CMF.

Thus, what is desirable are new methods for purifying a 5-(halomethyl)furfural composition or obtaining gaseous 5-(halomethyl)furfural at commercially viable operating conditions that decrease or minimize decomposition of the 5-(halomethyl)furfural.

BRIEF SUMMARY

The present disclosure addresses this need by providing methods for obtaining gaseous 5-(halomethyl)furfural or purifying a 5-(halomethyl)furfural composition in a way that can decrease or minimize decomposition of the 5-(halomethyl)furfural. The 5-(halomethyl)furfural may be 5-(chloromethyl)furfural or 5-(bromomethyl)furfural.

In one aspect, provided is a method that includes boiling a mixture having 5-(halomethyl)furfural and solvent to produce gaseous 5-(halomethyl)furfural. In some embodiments, the solvent may have a boiling point at or above the boiling point of the 5-(halomethyl)furfural. In certain embodiments where the 5-(halomethyl)furfural is 5-(chloromethyl)furfural, the solvent may have a boiling point of at least 240° C. at standard pressure (e.g., 1 atm).

In other aspect, provided is a method that includes contacting 5-(halomethyl)furfural with a stripping agent to produce gaseous 5-(halomethyl)furfural, wherein the stripping agent has a vapor pressure above the vapor pressure of 5-(halomethyl)furfural. In some embodiments, provided is a method that includes contacting a mixture comprising 5-(halomethyl)furfural and solvent with a stripping agent to produce gaseous 5-(halomethyl)furfural, wherein the stripping agent has a vapor pressure above the vapor pressure of 5-(halomethyl)furfural.

In some embodiments of the methods above, the solvent includes one or more aromatic solvents, one or more heavy alkane solvents, one or more ester solvents, one or more silicone oils, or any combinations or mixtures thereof. In certain embodiments, the solvent includes one or more alkyl phenyl solvents. In one embodiment, the solvent includes sulfolane, hexadecane, heptadecane, octadecane, icosane, heneicosane, docosane, tricosane, tetracosane, naphthalene, anthracene, tetramethylnaphthalene, or any combinations or mixtures thereof.

In some embodiments that may be combined with any of the foregoing embodiments, the method further includes collecting the gaseous 5-(halomethyl)furfural. In other embodiments that may be combined with any of the foregoing embodiments, the method further includes condensing the gaseous 5-(halomethyl)furfural to obtain purified 5-(halomethyl)furfural in liquid form. In yet other embodiments that may be combined with any of the foregoing embodiments, the method further includes depositing the gaseous 5-(halomethyl)furfural to obtain purified 5-(halomethyl)furfural in solid form.

Provided herein is also a system that includes: a purification apparatus; 5-(halomethyl)furfural; and solvent having a boiling point at or above the boiling point of the 5-(halomethyl)furfural. In some embodiments of the system, the solvent in the system may include one or more aromatic solvents, one or more heavy alkane solvents, one or more ester solvents, one or more silicone oils, or any combinations or mixtures thereof. In certain embodiments, the solvent includes one or more alkyl phenyl solvents. In one embodiment, the solvent includes sulfolane, hexadecane, heptadecane, octadecane, icosane, heneicosane, docosane, tricosane, tetracosane, naphthalene, anthracene, tetramethylnaphthalene, or any combinations or mixtures thereof. The purification apparatus may be configured for continuous or batch processing.

DESCRIPTION OF THE FIGURES

The present application can be best understood by reference to the following description taken in conjunction with the accompanying figures, in which like parts may be referred to by like numerals.

DETAILED DESCRIPTION

Figure 1:
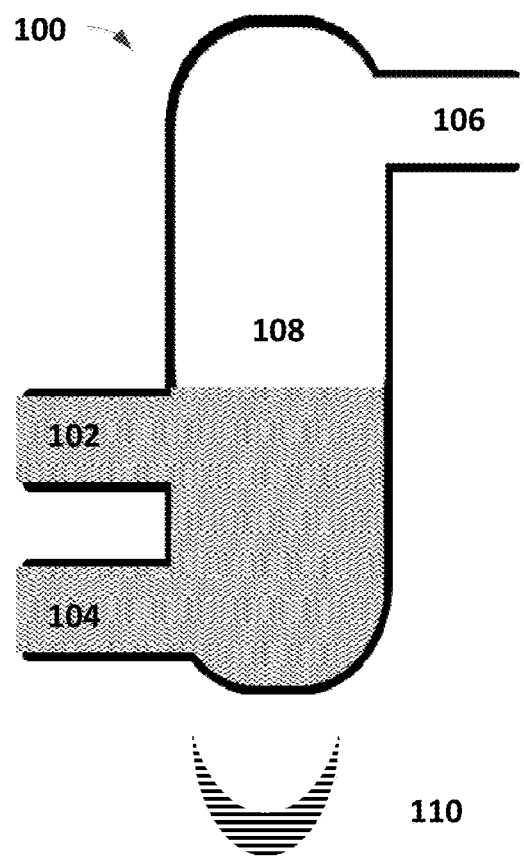
FIG. 1 depicts an exemplary apparatus suitable for continuous processing with the methods provided herein.

The following description sets forth exemplary methods, parameters and the like. It should be recognized, however, that such description is not intended as a limitation on the scope of the present disclosure but is instead provided as a description of exemplary embodiments.

In one aspect, provided is a method for obtaining gaseous 5-(halomethyl)furfural or purifying a 5-(halomethyl)furfural composition by boiling a mixture having 5-(halomethyl)furfural and particular solvents. In some embodiments, the solvent may have a boiling point at or above the boiling point of the 5-(halomethyl)furfural. In certain embodiments where the 5-(halomethyl)furfural is 5-(chloromethyl)furfural, the solvent may have a boiling point of at least 240° C. at standard pressure (e.g., 1 atm). Examples of suitable solvents may include, for example, alkyl phenyl solvents (e.g., linear alkyl benzenes), heavy alkane solvents, ester solvents, aromatic solvents, silicone oils, or any combinations or mixtures thereof. The 5-(halomethyl)furfural may be 5-(chloromethyl)furfural or 5-(bromomethyl)furfural.

In another aspect, provided is a method for obtaining gaseous 5-(halomethyl)furfural or purifying a 5-(halomethyl)furfural composition by gas stripping. In some embodiments, such method includes contacting a stripping agent with 5-(halomethyl)furfural to vaporize the 5-(halomethyl)furfural. In other embodiments, such method includes contacting a stripping agent with a mixture having 5-(halomethyl)furfural and the particular solvents described herein to vaporize the 5-(halomethyl)furfural in the 5-(halomethyl)furfural composition. The stripping agent used in this method has a vapor pressure above the vapor pressure of 5-(halomethyl)furfural.

The methods provided herein may be employed to produce gaseous 5-(halomethyl)furfural, or to purify a 5-(halomethyl)furfural composition, at conditions that can decrease or minimize decomposition of the 5-(halomethyl)furfural. Further, the 5-(halomethyl)furfural obtained by the methods described herein may be in liquid form or solid form, including crystalline forms. For example, in one variation, provided is a method for distilling 5-(halomethyl)furfural in the presence of the solvents described herein at conditions that can decrease or minimize decomposition of the 5-(halomethyl)furfural. It should be understood that distilling 5-(halomethyl)furfural involves boiling 5-(halomethyl)furfural to form gaseous 5-(halomethyl)furfural, and condensing or depositing the gaseous 5-(halomethyl)furfural in a liquid or solid form, respectively.

The gaseous 5-(halomethyl)furfural may be collected, condensed, deposited, or fed in its gaseous state into another reaction. The 5-(halomethyl)furfural composition, the methods, and the purified 5-(halomethyl)furfural obtained are each described in further detail below.

5-(Halomethyl)furfural Provided For Methods

The 5-(halomethyl)furfural provided for the methods described herein may be pure, such that the methods are employed to obtain a gaseous form 5-(halomethyl)furfural. The 5-(halomethyl)furfural provided for the methods described herein may also have one or more impurities, such that the methods are employed to separate the 5-(halomethyl)furfural from one or more of the impurities.

Any suitable sources (including any commercially available sources) and methods known in the art may be used to prepare 5-(halomethyl)furfural for use in the methods described herein. Methods known in the art to prepare 5-(halomethyl)furfural are described in, for example, U.S. Pat. No. 7,829,732; Fentorr & Gostling, *J. Chem. Soc.*, 1899, 75, 423; Haworth & Jones, *J. Chem. Soc.*, 1944, 667; Szmant & Chundury, *J. Chem. Tech. Biotechnol.* 1981, 31, 205-212; and Mascal and Nikitin, *ChemSusChem*, 2009, 2, 859-861; Brasholz et al., *Green Chem.*, 2011, 13, 1114-1117.

Feedstock

Feedstocks suitable for producing 5-(halomethyl)furfural may include any materials that contain six-carbon (C6) sugars. The C6 sugars may be monomeric, dimeric, or polymeric. It should be understood that "six-carbon sugars" or "C6 sugars" refer to sugars where the monomeric unit has six carbons. Moreover, the C6 sugars have alcohol groups needed for conversion into 5-(halomethyl)furfural.

In one embodiment, the C6 sugars can be cellulose or provided in hemicellulose. One of skill in the art would recognize that cellulose and hemicellulose can be found in biomass (e.g., cellulosic biomass or lignocellulosic biomass). Biomass can be any plant material made up of organic compounds relatively high in oxygen, such as carbohydrates, and also contain a wide variety of other organic compounds. The biomass may also contain other materials that are not converted to 5-(halomethyl)furfural, such as inorganic salts and clays.

Biomass may be pretreated to help make the sugars in the biomass more accessible, by disrupting the crystalline structures of cellulose and hemicellulose and breaking down the lignin structure (if present). Common pretreatments known in the art involve, for example, mechanical treatment (e.g., shredding, pulverizing, grinding), concentrated acid, dilute acid, $SO_2$, alkali, hydrogen peroxide, wet-oxidation, steam explosion, ammonia fiber explosion (AFEX), supercritical $CO_2$ explosion, liquid hot water, and organic solvent treatments.

Biomass may originate from various sources. For example, biomass may originate from agricultural materials (e.g., corn stover, rice hulls, peanut hulls, spent grains), processing waste (e.g., paper sludge), and recycled cellulosic materials (e.g., cardboard, old corrugated containers (OCC), old newspaper (ONP), or mixed paper). Other examples of suitable biomass may include wheat straw, paper mill effluent, newsprint, municipal solid wastes, wood chips, forest thinings, slash, miscanthus, switchgrass, sorghum, bagasse, manure, wastewater biosolids, green waste, and food/feed processing residues.

In other embodiments, the C6 sugars can be glucose, fructose (e.g., high fructose corn syrup), cellobiose, sucrose, lactose, and maltose. Any stereoisomers of such C6 sugars may also be used in the methods described herein.

In yet other embodiments, the feedstock may be a saccharide composition. For example, the sugar composition may include a single saccharide or a mixture of saccharides such as fructose, glucose, sucrose, lactose and maltose.

Impurities

Methods known in the art to prepare 5-(halomethyl)furfural typically yield one or more impurities in the product mixture. These impurities may be bi-products and/or residual starting materials, or any decomposition or degradation products thereof, from the reaction(s) used to prepare 5-(halomethyl)furfural.

For example, 5-(chloromethyl)furfural prepared from cellulosic materials according to the methods described in U.S. Pat. No. 7,829,732 can yield bi-products such as 2-(2-hydroxyacetyl)furan, 5-(hydroxymethyl)furfural, levulinic acid, and humic materials. Examples of other bi-products and decomposition or degradation products may include furfural and formic acid. Examples of residual starting materials may include residual sugars (e.g., C5 monomeric sugars, C6 monomeric sugars, C5 oligomeric sugars, C6 oligomeric sugars), residual biomass (e.g., corn stover, old corrugated containers, old newspaper). Examples of residual reagents may include residual acid (e.g., hydrochloric acid). One or more the bi-products, residual starting materials, and residual reagents, and any decomposition or degradation products thereof, may be part of the 5-(halomethyl)furfural composition that is provided for the methods described herein.

Thus, in some embodiments, the one or more impurities present in the 5-(halomethyl)furfural composition provided for the methods herein include 2-(2-hydroxyacetyl)furan, 5-(hydroxymethyl)furfural, levulinic acid, humic materials, furfural, formic acid, residual sugars (e.g., C5 monomeric sugars, C6 monomeric sugars, C5 oligomeric sugars, C6 oligomeric sugars), residual biomass (e.g., corn stover, old corrugated containers, old newspaper), and/or residual acid (e.g., hydrochloric acid).

In certain embodiments, the 5-(halomethyl)furfural composition used in the methods herein has less than 5 wt %, less than 4 wt %, less than 3 wt %, less than 2 wt %, less than 1 wt %, less than 0.5 wt %, less than 0.4 wt %, less than 0.3 wt %, less than 0.2 wt %, less than 0.1 wt %, less than 0.01 wt %, less than 0.05 wt %, less than 0.001 wt % of acid (e.g., hydrochloric acid). The acid present in the 5-(halomethyl) furfural composition may be residual from the reaction used to prepare the 5-(halomethyl)furfural, or may be the result of decomposition or degradation of 5-(halomethyl)furfural. It should be understood that the 5-(halomethyl)furfural composition used in the methods described herein may be washed (e.g., with a brine solution) to decrease the amount of acid present in the composition.

The 5-(halomethyl)furfural composition used in the methods herein may be in liquid or solid form, or a combination thereof. In one embodiment, the 5-(halomethyl)furfural composition is in liquid form. In another embodiment, the 5-(halomethyl)furfural composition is in solid form.

Boiling

Gaseous 5-(halomethyl)furfural may be obtained, or a 5-(halomethyl)furfural composition may be purified, using certain solvents at operating conditions that can decrease or minimize decomposition or degradation of the 5-(halomethyl)furfural.

The 5-(halomethyl)furfural and the solvent may be provided to the apparatus separately or together. For example, when the 5-(halomethyl)furfural and the solvent are both in liquid form, they may be provided to the apparatus as individual feed streams or as a combined feed stream.

Further, in some embodiments, the 5-(halomethyl)furfural, the solvent, or both may be heated to the operating temperature or close to the operating temperature before they are provided (either separately or together) to the apparatus. The heat source may serve to primarily maintain the operating temperature of the apparatus. In other embodiments, the 5-(halomethyl)furfural, the solvent, or both may be provided to the apparatus (either separately or combined) at or below the operating temperature, and then heated to the operating temperature using the heat source. In yet other embodiments, the 5-(halomethyl)furfural, the solvent, or both may be heated above the operating temperature before they are provided (either separately or together) for flash distillation, where the pre-heated 5-(halomethyl)furfural and/or the solvent may be subjected to an operating pressure below the vapor pressure of the 5-(halomethyl)furfural to cause boiling.

Solvents

The solvents used may be obtained from any source, including any commercially available source. In some embodiments, the solvents used herein have a boiling point at or above the boiling point of the 5-(halomethyl)furfural. In some embodiments, the solvent has a boiling above the boiling point of the 5-(halomethyl)furfural. The boiling points may be determined at any pressure, for example, at the operating pressure.

The boiling point of a substance is the temperature at which the vapor pressure of the substance equals the pressure surrounding the liquid (e.g., in the apparatus), and the liquid changes into a vapor. Boiling is vaporization of a liquid when the liquid is heated to or above its boiling point, and/or when the pressure of the liquid is reduced to or below its vapor pressure. Further, one of skill would recognize that the boiling point of a liquid varies depending on the surrounding environmental pressure (e.g., in the apparatus). For example, a liquid in a vacuum has a lower boiling point than when that liquid is at atmospheric pressure. The boiling points of a substance (such as 5-(halomethyl)furfural) at a given pressure may be determined by any suitable methods known in the art.

It is intended and understood that the boiling point of the solvent and the boiling point of the 5-(halomethyl)furfural used in selecting the solvent are measured in the absence of the 5-(halomethyl)furfural composition. By way of an example, the selection of the solvent may be based on the boiling point of the solvent before the solvent has been fed into the apparatus and combined with the 5-(halomethyl) furfural composition.

In certain embodiments, the boiling point of the solvent is at least 20° C., at least 30° C., at least 40° C., at least 50° C., at least 60° C., at least 70° C., at least 80° C., at least 90° C., at least 100° C., at least 150° C., at least 200° C., at least 250° C. or at least 300° C. above the boiling point of the 5-(halomethyl)furfural at the operating pressure for the distillation. In particular embodiments, the boiling point of the solvent is between 20° C. and 500° C., between 20° C. and 300° C., between 20° C. and 200° C., between 20° C. and 100° C., between 50° C. and 300° C., or between 100° C. and 300° C. above the boiling point of the 5-(halomethyl) furfural at the operating pressure.

In certain embodiments where the 5-(halomethyl)furfural is 5-(chloromethyl)furfural, the solvent may have a boiling point of at least 240° C., at least 245° C., at least 250° C., or at least 255° C. at standard pressure (e.g., 1 atm).

In some embodiments, the solvents suitable for use in the methods provided herein at least partially dissolve 5-(halomethyl)furfural.

In other embodiments, the solvents suitable for use in the methods provided herein may include, for example, aromatic solvents (including alkyl phenyl solvents), alkyl solvents, halogenated solvents, silicone oils, or any combinations or mixtures thereof, that have a boiling point or a boiling point range above the boiling point of 5-(halomethyl)furfural. It should be understood that a solvent may fall within one or more classes described above. For example, Wibaryl® A is an aromatic solvent, that can more specifically be classified as an alkyl phenyl solvent.

In certain embodiments, the solvent may include one or more alkyl phenyl solvents, such as one or more linear alkyl benzenes. As used herein, "an alkyl phenyl solvent" refers to a class of solvents that have one or more alkyl chains attached to one or more phenyl or phenyl-containing ring systems. The alkyl phenyl solvent may be referred to as an alkylbenzene or a phenylalkane. One skilled in the art would recognize that certain phenylalkanes may also be interchangeably referred to as an alkylbenzene. For example, (1-phenyl)dodecane and dodecylbenzene refer to the same solvent.

In certain embodiments, the solvent includes one or more alkylbenzenes. Examples may include (monoalkyl)benzenes, (dialkyl)benzenes, and (polyalkyl)benzenes. In certain embodiments, the alkylbenzene has one alkyl chain attached to one benzene ring. The alkyl chain may have one or two points of attachment to the benzene ring. Examples of alkylbenzenes with one alkyl chain having one point of attachment to the benzene ring include dodecylbenzene. In embodiments where the alkyl chain has two points of attachment to the benzene ring, the alkyl chain may form a fused cycloalkyl ring to the benzene. Examples of alkylbenzenes with one alkyl having two points of attachment to the benzene ring include tetralin. It should be understood that the fused cycloalkyl ring may be further substituted with one or more alkyl chains.

In other embodiments, the alkylbenzene has two or more alkyl chains (e.g., 2, 3, 4, 5, or 6 alkyl chains) attached to one benzene ring.

In yet other embodiments, the alkylbenzene is an alkyl-substituted fused benzene ring system. The fused benzene ring system may include benzene fused with one or more heterocyclic rings. In one embodiment, the fused benzene ring system may be two or more fused benzene rings, such as naphthalene. The fused benzene ring system may be optionally substituted by one or more alkyl chains. For example, such alkyl-substituted fused benzene ring system may include tetramethylnaphthalene.

In some embodiments, the solvent includes phenylalkane. Examples may include (monophenyl)alkanes, (diphenyl)alkanes, and (polyphenyl)alkanes. In certain embodiments, the phenylalkane has one phenyl ring attached to one alkyl chain. In one embodiment, the alkyl chain attached to the phenyl ring may be an alkyl chain with at least eight carbons (e.g., $C_{8+}$ alkyls), such as a $C_{8-20}$ alkyl or a $C_{13-20}$ alkyl. The phenyl ring may be attached to any carbon along the alkyl chain. For example, the phenyl alkyl having one alkyl chain may be (1-phenyl)dodecane or (2-phenyl)dodecane.

In other embodiments, the phenylalkane has two or more phenyl rings attached to one alkyl chain.

The alkyl phenyl solvents may be linear or branched, based on the alkyl chain(s) attached to the phenyl or phenyl-containing ring systems. "Alkyl" refers to a monoradical saturated hydrocarbon chain. The length of the alkyl chain may vary. In certain embodiments, the alkyl chain may be 1 to 20 carbon atoms (e.g., $C_{1-20}$ alkyl). In one embodiment, the alkyl chain may be 4 to 15 carbons (e.g., $C_{4-15}$ alkyl), 8 to 20 carbons (e.g., $C_{8-20}$ alkyl), or 10 to 13 carbons (e.g., $C_{10-13}$ alkyl).

The alkyl chain may be linear or branched. Linear alkyl chains may include, for example, n-propyl, n-butyl, n-hexyl, n-heptyl, n-octyl, n-nonanyl, n-decyl, n-undecyl, and n-dodecyl. Branched alkyl chains may include, for example, isopropyl, sec-butyl, isobutyl, tert-butyl, and neopentyl. In some embodiments where the solvent includes two or more alkyl chains, certain alkyl chains may be linear, whereas other alkyl chains may be branched. In other embodiments where the solvent includes two or more alkyl chains, all the alkyl chains may be linear or all the alkyl chains may be branched.

For example, the solvent may include one or more linear alkylbenzenes ("LABs"). Linear alkylbenzenes are a class of solvents having the formula $C_6H_5C_nH_{2n+1}$. For example, in one embodiment, the linear alkylbenzene is dodecylbenzene. Dodecylbenzene is commercially available, and may be "hard type" or "soft type". Hard type dodecylbenzene is a mixture of branched chain isomers. Soft type dodecylbenzene is a mixture of linear chain isomers. In one embodiment, the solvent includes hard type dodecylbenzene.

In some embodiments, the solvent may include any of the alkyl phenyl solvents described above, in which the phenyl ring is substituted with one or more halogen atoms. In certain embodiments, the solvent includes an alkyl(halobenzene). For example, the alkyl(halobenzene) may include alkyl(chlorobenzene). In one embodiment, the halo substituent for the phenyl ring may be, for example, chloro, bromo, or any combination thereof.

In some embodiments, the solvent may include one or more heavy alkanes. "Heavy alkanes" include saturated hydrocarbon chains containing at least 8 carbon atoms (e.g., $C_{8+}$ alkane), at least 10 carbon atoms (e.g., $C_{10+}$ alkane), or at least 13 carbon atoms (e.g., $C_{13+}$ alkane). In some embodiments, the heavy alkane may have 8 to 100 carbon atoms (e.g., $C_{8-100}$ alkanes), 8 to 50 carbon atoms (e.g., $C_{8-50}$ alkanes), 8 to 25 carbon atoms (e.g., $C_{8-25}$ alkanes), or 10 to 20 carbon atoms (e.g., $C_{10-20}$ alkanes). In other embodiments, the solvent may include one or more heavy alkanes, wherein at least one heavy alkane has at least 13 carbon atoms. In one embodiment, the solvent may include hexadecane, heptadecane, octadecane, icosane, heneicosane, docosane, tricosane, tetracosane, or any combinations or mixtures thereof.

In other embodiments, the solvent may include one or more esters. In some embodiments, the esters may be fatty acids. In certain embodiments, the esters may be (heavy alkyl)-esters, e.g., $C_{8+}$ alkyl-(O)OH. In some embodiments, the (heavy alkyl)-esters may have 8 to 100 carbon atoms (e.g., $C_{8-100}$ alkyl-(O)OH), 8 to 50 carbon atoms (e.g., $C_{8-50}$ alkyl-(O)OH), 8 to 25 carbon atoms (e.g., $C_{8-25}$ alkyl-(O)OH), or 10 to 20 carbon atoms (e.g., $C_{10-20}$ alkyl-(O)OH). In one embodiment, the solvent may include hexadecanoic acid.

In other embodiments, the solvent may include one or more aromatic solvents. In some embodiments, the aromatic solvent is a $C_{6-20}$ aromatic solvent, or a $C_{6-15}$ aromatic solvent. In one embodiment, the solvent includes naphthalene, naphthenic oil, alkylated naphthalene, diphenyl, polychlorinated biphenyls, polycyclic aromatic hydrocarbons, or any combinations or mixtures thereof.

In yet other embodiments, the solvent may include one or more silicone oils. In certain embodiments, the solvent includes one or more alkyl siloxanes.

The solvent may be a single solvent or may include a mixture of solvents. If the solvent is a mixture of solvents, the solvent mixture has a boiling point at or above the boiling point of the 5-(halomethyl)furfural at the operating pressure. For example, in some embodiments, the solvent may be a mixture of (i) one or more alkyl phenyl solvents, and (ii) one or more aromatic solvents. For example, in another embodiment, the solvent may be a mixture of toluene and one or more other solvents such as camphor, anthracene, and anthraquinone. It should be understood that if the solvent mixture has a range of boiling points, such range may encompass the boiling point of the 5-(halomethyl)furfural at the operating pressure but the entire range need not be above the boiling point of the 5-(halomethyl)furfural at the operating pressure.

It should also be understood that the solvent may include any substance that is a liquid at the operating temperature and pressure, but such substance may not be a liquid at standard temperature and pressure.

Exemplary solvents that may be used in the methods and compositions described herein include alkyl benzenes, sulfolane, heavy alkanes, diphenyl ethers and polyphenyl ethers, and other aromatic solvents. In certain embodiments, the solvent includes alkyl benzenes. In one embodiment, the solvent includes dodecylbenzene. An example of such dodecylbenzene is Marlican®. In other embodiments, the alkyl benzene may have alkyl side chains having at least 10 carbon atoms, at least 13 carbon atoms, or 10 to 40 carbon atoms, or 10 to 20 carbon atoms, or 10 to 13 carbon atoms, or 13 to 30 carbon atoms. Suitable alkyl benzenes may include, for example, Wibaryl® (e.g., benzene substituted with $C_{10-13}$ alkyl chain), Wibaryl® F (heavy alkylate), Wibaryl® A (diphenylalkanes, wherein the alkyl chains are $C_{10-13}$ alkyl chains), Wibaryl® B (dialkylbenzenes, wherein the alkyl chains are $C_{10-13}$ alkyl chains), Wibaryl® AB (a mixture of diphenylalkanes and dialkylbenzenes), Wibaryl® R (oligo- and polyalkylbenzenes), Cepsa Petrelab® 500-Q (linear alkylbenzene containing side alkyl chains of 10-13 carbon atoms), Cepsa Petrelab® 550-Q (linear alkylbenzene containing side alkyl chains of 10-13 carbon atoms), Cepsa Petrene® 900-Q (heavy alkylbenzene containing primarily dialkylbenzenes), Synnaph® AB 3 (heavy alkyl benzene), Synnaph® DAB4 (dialkylbenzene), and Therminol® 55 (benzene substituted with $C_{13-30}$ alkyl chains).

In other embodiments, the solvent includes phenyl ethers, including monophenyl ethers, diphenyl ethers and polyphenyl ethers. Suitable phenyl ethers include, for example, Santovac® 5 and Santovac® 7. In yet other embodiments, the solvent includes other aromatic solvents. The aromatic solvent may include at least one alkyl chain substituent, and such aromatic solvents may include monocyclic aromatic ring system or bicyclic or polyciclic aromatic systems (including fused ring systems). Examples of such aromatic solvents include, for example, naphthalene, anthracene, Dowtherm® (mixture of biphenyl and diphenyl oxide), Dowtherm® G (di- and tri-aryl ethers), Dowtherm® Q (a mixture of diphenylethane and alkylated aromatics), and Dowtherm® MX (a mixture of alkylated aromatics). As discussed above, any combinations or mixtures of such solvents may also be used.

Operating Conditions

When the solvents described above are used, the methods to obtain gaseous 5-(halomethyl)furfural or to purify 5-(halomethyl)furfural may be performed at pressures that are higher than what are currently used in the art.

The operating pressure refers to the pressure in the apparatus at the interface between the bottoms liquid and the gas phase. In some embodiments, the operating pressure is at least 30 torr, at least 50 torr, at least 100 torr, at least 125 torr, at least 150 torr, at least 200 torr, or at least 250 torr. In certain embodiments, the operating pressure is between 50 torr and 2000 torr, between 50 torr and 1250 torr, between 100 torr and 1400 torr, between 100 torr and 1000 torr, between 100 torr and 800 torr, between 100 torr and 400 torr, between 125 torr and 350 torr, between 150 torr and 250 torr, between 50 and 500 torr, or between 50 torr and 300 torr.

The operating temperature refers to the temperature in the apparatus at the interface between the bottoms liquid and the gas phase. As discussed in further detail below, the apparatus may be configured with an external heat source, an internal heat source, or a combination thereof. For example, the apparatus may be configured with an external heat source, such as a heat exchanger. The apparatus may also be configured with an internal heat source, such as a heat coil.

In some embodiments, the operating temperature is at least 60° C., at least 70° C., at least 80° C., at least 100° C., at least 150°, or least 200° C. In certain embodiments, the operating temperature is between 60° C. and 400° C., between 80° C. and 350° C., between 80° C. and 300° C., between 80° C. and 200° C., between 100° C. and 180° C., or between 120° C. and 160° C.

While pressure has been described in torr and temperature as degrees Celsius, one of skill in the art would be able to convert the pressure and temperature units to other commonly known units. For example, temperature may be expressed as Kelvin. Pressure may also be expressed as bar, atmosphere (atm), pascal (Pa) or pound-force per square inch (psi).

Gas Stripping

Gaseous 5-(halomethyl)furfural may be obtained, or 5-(halomethyl)furfural may be purified, by gas stripping using a stripping agent at operating conditions that can decrease or minimize decomposition or degradation of the 5-(halomethyl)furfural. In some embodiments, gas stripping may be performed in the absence of the solvents described herein. In other embodiments, gas stripping is performed with the solvents described herein.

Stripping Agent

A stripping agent may be fed to the apparatus and contacted with the 5-(halomethyl)furfural composition to vaporize the 5-(halomethyl)furfural. The stripping agent can be any substance that has a vapor pressure at or above the vapor pressure of 5-(halomethyl)furfural, and may be obtained from any source, including any commercially available source.

The stripping agent may be provided to the apparatus as a gas or a liquid. In one embodiment, the stripping agent is a gas. In some embodiments, the gas may be provided to the apparatus separately from the 5-(halomethyl)furfural composition. For example, the gas may be an inert gas (e.g., nitrogen, argon, helium, or any combinations or mixtures thereof).

In other embodiments, the stripping agent may be a gas that is dissolved or partially dissolved in the 5-(halomethyl)furfural composition provided to the apparatus.

In yet other embodiments, the stripping agent may include any substance that is a gas at the operating temperature and pressure, but such substance may not be a gas at standard temperature and pressure. For example, the stripping agent may be a liquid that has a vapor pressure at or above the vapor pressure of 5-(halomethyl)furfural at the operating conditions. In one embodiment, the stripping agent may be toluene, which is gaseous at operating conditions (e.g., 100° C. and 100 torr), but is a liquid at standard temperature and pressure.

The stripping agent may be a single substance or may include a mixture of substances. If the stripping agent is a mixture of substances, the mixture at the operating conditions has a vapor pressure above the vapor pressure of the 5-(halomethyl)furfural. It should be understood that if the solvent mixture has a range of vapor pressures, such range may encompass the vapor pressure of the 5-(halomethyl)furfural at the operating pressure but the entire range need not be above the vapor pressure of the 5-(halomethyl)furfural at the operating pressure.

It should be understood that in certain exemplary embodiments, the 5-(halomethyl)furfural composition and the particular solvents described herein may be combined and contacted with the stripping agent to obtain gaseous 5-(halomethyl)furfural or to purify 5-(halomethyl)furfural.

Solvents

Any of the solvents described above may be used for the gas stripping method. For example, the solvents suitable for use in the gas stripping method may include alkyl phenyl solvents, aromatic solvents, alkyl solvents, halogenated solvents, silicone oils, or any combinations or mixtures thereof, that have a boiling point or a boiling point range above the boiling point of 5-(halomethyl)furfural. In certain embodiments, the solvent may include one or more alkyl phenyl solvents, such as one or more linear alkyl benzenes.

Operating Conditions

When gas stripping as described above is employed, the method may be performed at operating conditions that may decrease or minimize decomposition of the 5-(halomethyl) furfural.

In some embodiments, the operating temperature is at least 60° C., at least 70° C., at least 80° C., at least 100° C., at least 150°, or least 200° C. In certain embodiments, the operating temperature is between 80° C. and 400° C., between 80° C. and 300° C., between 80° C. and 250° C., between 80° C. and 240° C., between 80° C. and 200° C., 100° C. and 180° C., or between 120° C. and 160° C.

In some embodiments, the operating pressure is at least 30 torr, at least 50 torr, at least 100 torr, at least 125 torr, at least 150 torr, at least 200 torr, or at least 250 torr. In certain embodiments, the operating pressure is between 50 torr and 10,000 torr, between 50 torr and 9000 torr, between 50 torr and 8000 torr, between 50 torr and 7000 torr, between 50 torr and 6000 torr, between 50 torr and 5000 torr, between 50 torr and 4000 torr, between 50 torr and 3000 torr, between 100 torr and 10,000 torr, between 100 torr and 4000 torr, between 100 torr and 3000 torr, between 100 torr and 2000 torr, between 100 torr and 400 torr, between 125 torr and 350 torr, or between 150 torr and 250 torr.

5-(Halomethyl)furfural Obtained from Methods

In some aspects, the methods described herein produce gaseous 5-(halomethyl)furfural. The gaseous 5-(halomethyl) furfural may be collected, condensed, deposited, or fed in a gaseous state into another reaction.

In some embodiments, the gaseous 5-(halomethyl)furfural may be collected in any suitable vessel, where the gaseous 5-(halomethyl)furfural may be stored for further use at a later time.

In other embodiments, the gaseous 5-(halomethyl)furfural may be condensed to obtain 5-(halomethyl)furfural in liquid form. Any suitable methods or systems known in the art to condense a gas to a liquid may be used, including for example, a condenser.

In yet other embodiments, the gaseous 5-(halomethyl) furfural may be deposited to obtain 5-(halomethyl)furfural in solid form. Any suitable methods or systems known in the art to deposit a gas to obtain a solid may be used. Where solid 5-(halomethyl)furfural is produced, the solid nature of the product may make it easier to handle than product in liquid form (including, for example, oil). For example, the solid 5-(halomethyl)furfural can more easily and conveniently be stored and transported. The solid 5-(halomethyl) furfural obtained may be amorphous or crystalline.

In yet other embodiments, the gaseous 5-(halomethyl) furfural may be collected in a reflux system and fed back into the system to maintain equilibrium in the apparatus. For example, a reflux system may be used when the apparatus is a distillation column that includes trays or packing materials.

Purity

The 5-(halomethyl)furfural obtained may have an increased overall purity. One of skill in the art would recognize the various methods and techniques to measure the purity of a sample. For example, components in the sample can be identified and the amounts of such components can be measured by high-performance liquid chromatography (also known in the art as high-pressure liquid chromatography or HPLC), gas chromatography-mass spectrometry (GS-MS), magnetic resonance spectroscopy (e.g., $^1$H-NMR, $^{13}$C-NMR), differential scanning calorimetry (DSC), or any combinations of such methods.

In some embodiments, the 5-(halomethyl)furfural obtained from the methods provided herein may have a purity of at least 90%, at least 95%, at least 96%, at least 97%, at least 98%, at least 99%, at least 99.5%, or at least 99.9%. In one embodiment, the 5-(halomethyl)furfural obtained from the methods provided herein has a purity between 95% and 100%, between 95% and 99%, between 98% and 100%, or about 95%, about 96%, about 97%, about 98%, about 99%, or about 100%.

Distillation/Stripping Yield

The methods provided herein may produce 5-(halomethyl)furfural with a distillation yield or stripping yield (as the case may be depending on the method employed) of at least 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, or 99 wt %, or between 10 wt % and 99 wt %, between 50 wt % and 99 wt %, between 60 wt % and 99 wt %, or between 70 wt % and 90 wt %. Distillation yield or the stripping yield is the ratio of the amount of 5-(halomethyl) furfural collected to the amount of 5-(halomethyl)furfural provided to the apparatus. In certain instances where 5-(halomethyl)furfural is collected in a receiving flask, the distillation yield is the ratio of the amount of 5-(halomethyl) furfural collected in the receiving flask at the end of the process to the amount of 5-(halomethyl)furfural provided to the still flask at the beginning of the process. In other instances where a continuous process is employed, the distillation yield may be the ratio of the amount of condensed or deposited 5-(halomethyl)furfural to the amount of 5-(halomethyl)furfural fed to the apparatus.

It should be understood that reference to "about" a value or parameter herein includes (and describes) embodiments that are directed to that value or parameter per se. For example, description referring to "about x" includes description of "x" per se. In other instances, the term "about" when used in association with other measurements, or used to modify a value, a unit, a constant, or a range of values, refers to variations of +/−5%.

It should also be understood that reference to "between" two values or parameters herein includes (and describes) embodiments that include those two values or parameters per se. For example, description referring to "between x and y" includes description of "x" and "y" per se.

Downstream Products

The 5-(halomethyl)furfural produced according to the methods described herein may be used in other chemical reactions, or further processed into other furanic derivatives for biofuels, diesel additives, or plastics. For example, CMF may be converted into dimethylfuran and ethoxymethylfurfural using methods known in the art.

Apparatus

Any suitable apparatus may be used in the methods described herein. The methods may be performed in a continuous or batch apparatus.

With reference to FIG. 1, an exemplary continuous apparatus is depicted. Apparatus 100 has column 108, with feed inlet 102, bottoms outlet 104, and vapor outlet 106. In an exemplary process that may utilize apparatus 100, the 5-(halomethyl)furfural (in liquid form) and solvent are provided to column 108 via feed inlet 102 (either as individual feed streams or as a combined feed stream). The 5-(halomethyl) furfural and solvent form a mixture in column 108, and may be heated by external heating device 110 to a temperature suitable to boil the mixture in column 108 to produce gaseous 5-(halomethyl)furfural. It should be understood that an internal heating device may also be used in the alternative, or in combination with heating device 110. The gaseous 5-(halomethyl)furfural produced exits through vapor outlet 106, leaving behind the bottoms from the mixture. The bottoms may include, for example, the solvent and any impurities that may have been present in the 5-(halomethyl)furfural provided. The bottoms remaining in column 108 may be removed via bottoms outlet 104. The 5-(halomethyl)furfural, and optionally additional solvent, may be continuously added to the apparatus via feed inlet 102, while the gaseous 5-(halomethyl)furfural is continuously removed via vapor outlet 106.

Figure 2:
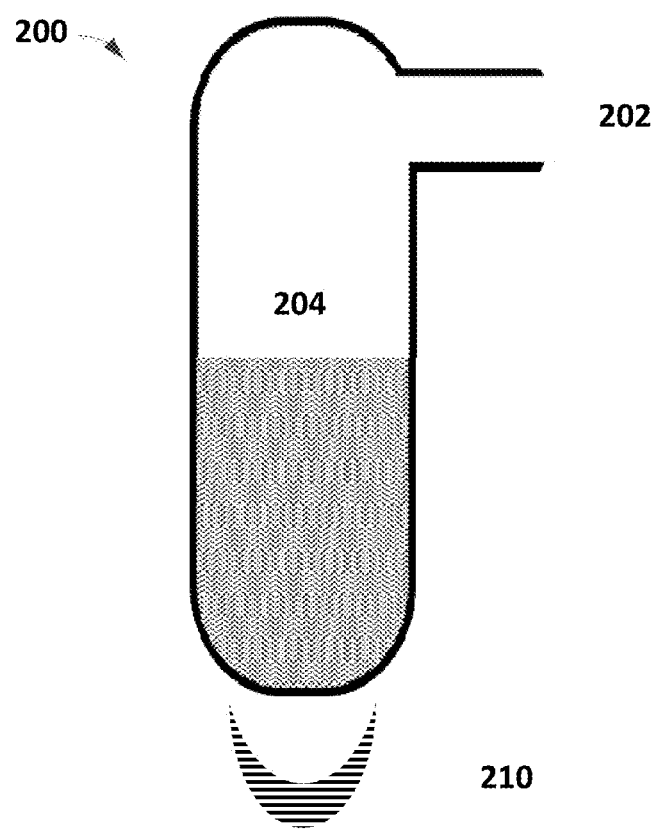
FIG. 2 depicts an exemplary apparatus suitable for batch processing with the methods provided herein.

With reference to FIG. 2, an exemplary batch apparatus is depicted. Apparatus 200 has column 204, with inlet/outlet 202. In an exemplary process that may utilize apparatus 200, the 5-(halomethyl)furfural (in liquid form) and solvent are provided to column 204 via inlet/outlet 202 (either as individual feed streams or as a combined feed stream). The 5-(halomethyl)furfural and solvent form a mixture in column 204, and may be heated by external heating device 210 to a temperature suitable to boil the mixture in column 204 to produce gaseous 5-(halomethyl)furfural. As discussed above, it should be understood that an internal heating device may also be used in the alternative, or in combination with heating device 210. The gaseous 5-(halomethyl)furfural produced exits through inlet/outlet 202, leaving behind the bottoms from the mixture.

Figure 3:
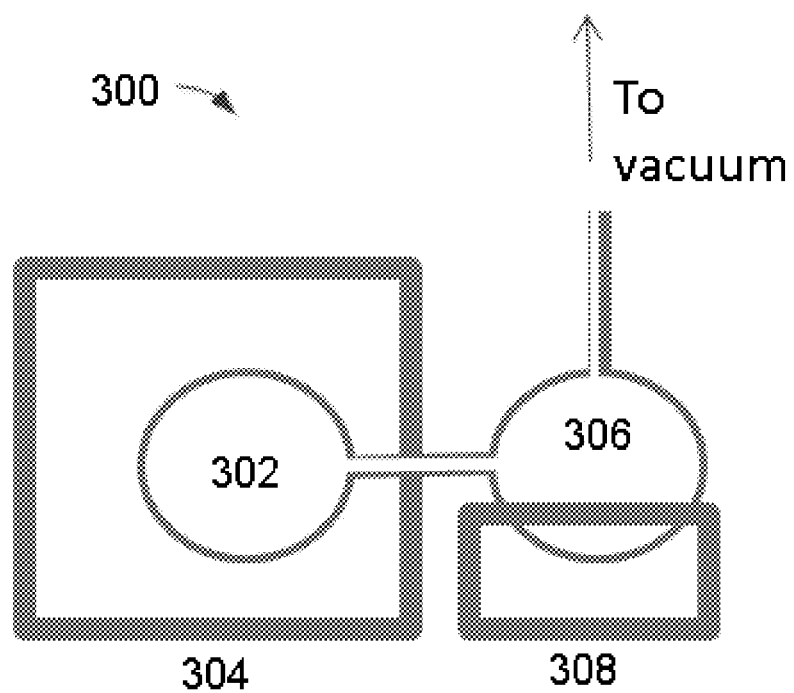
FIG. 3 depicts another exemplary apparatus for the methods provided herein.

With reference to FIG. 3, another exemplary apparatus is depicted. Apparatus 300 has still flask 302 connected to receiving flask 306 (also known in the art as the distillate flask). Crude 5-(halomethyl)furfural is provided to still flask 302, which is heated by heat source 304. The heat source may, for example, be an oven. When heated, a vapor phase that includes 5-(halomethyl)furfural is formed, and such vapor phase enters receiving flask 306, where the vapor phase is cooled by a cooling source 308 to obtain purified 5-(halomethyl)furfural. The cooling source may, for example, be a cool bath. It should be understood that, as depicted in FIG. 3, vacuum is connected to receiving flask 306 so that volatile materials (e.g., the gaseous 5-(halomethyl)furfural) flow into receiving flask 306.

The apparatus described above may include one or more additional components. For example, the apparatus may have a demister that prevents liquid droplets from leaving the vapor outlet. The apparatus may have an inlet diffuser to increase the surface area of the feed (e.g., the liquid 5-(halomethyl)furfural).

Other apparatuses may be used for the methods described herein. For example, in one embodiment, the apparatus may include one or more trays. In another embodiment, the apparatus may be a fractional distillation column. In yet another embodiment, the apparatus may include packaging. In yet another embodiment, the apparatus may be a flash drum, wherein the feed stream may be saturated with 5-(halomethyl)furfural. In yet another embodiment, the apparatus may be a wiped film evaporator, wherein the feed stream includes 5-(halomethyl)furfural.

Thus, provided are also systems that include any of the apparatus described above; 5-(halomethyl)furfural; and any of the solvents described herein.

ENUMERATED EMBODIMENTS

The following enumerated embodiments are representative of some aspects of the invention.

1. A method comprising boiling a mixture comprising 5-(halomethyl)furfural and solvent to produce gaseous 5-(halomethyl)furfural, wherein the solvent has a boiling point at or above the boiling point of the 5-(halomethyl)furfural.
2. A method comprising contacting a mixture comprising 5-(halomethyl)furfural and solvent with a stripping agent to produce gaseous 5-(halomethyl)furfural, wherein the stripping agent has a vapor pressure above the vapor pressure of 5-(halomethyl)furfural.
3. The method of embodiment 2, wherein the stripping agent is an inert gas.
4. The method of embodiment 2, wherein the stripping agent is hydrogen, nitrogen, argon, helium, or any combinations or mixtures thereof.
5. The method of any one of embodiments 1 to 4, wherein the method is performed at an operating pressure of at least 20 torr.
6. The method of embodiment 5, wherein the method is performed at an operating pressure of between 30 torr and 2000 torr.
7. The method of any one of embodiments 1 to 6, wherein the solvent comprises one or more aromatic solvents, one or more heavy alkane solvents, one or more ester solvents, one or more silicone oils, or any combinations or mixtures thereof.
8. The method of any one of embodiments 1 to 6, wherein the solvent comprises one or more alkyl phenyl solvents.
9. The method of any one of embodiments 1 to 6, wherein the solvent comprises dodecylbenzene, diphenyl ether, sulfolane, hexadecane, heptadecane, octadecane, icosane, heneicosane, docosane, tricosane, tetracosane, naphthalene, anthracene, tetramethylnaphthalene, or any combinations or mixtures thereof.
10. The method of any one of embodiments 1 to 9, further comprising condensing the gaseous 5-(halomethyl)furfural to obtain 5-(halomethyl)furfural in liquid form.
11. The method of any one of embodiments 1 to 9, further comprising depositing the gaseous 5-(halomethyl)furfural to obtain 5-(halomethyl)furfural in solid form.
12. The method of any one of embodiments 1 to 11, wherein the 5-(halomethyl)furfural is 5-(chloromethyl)furfural.
13. The method of any one of embodiments 1 to 12, wherein the 5-(halomethyl)furfural is provided in a 5-(halomethyl)furfural composition, and wherein the 5-(halomethyl)furfural composition has less than 5 wt % of acid.
14. A system comprising:
    a purification apparatus;
    5-(halomethyl)furfural; and
    solvent, wherein the solvent has a boiling point at or above the boiling point of the 5-(halomethyl)furfural.
15. The system of embodiment 14, wherein the solvent comprises one or more aromatic solvents, one or more heavy alkane solvents, one or more ester solvents, one or more silicone oils, or any combinations or mixtures thereof.
16. The system of embodiment 14, wherein the solvent comprises one or more alkyl phenyl solvents.
17. The system of embodiment 14, wherein the solvent comprises dodecylbenzene, diphenyl ether, sulfolane, hexadecane, heptadecane, octadecane, icosane, heneicosane, docosane, tricosane, tetracosane, naphthalene, anthracene, tetramethylnaphthalene, or any combinations or mixtures thereof.
18. The system of any one of embodiments 14 to 17, wherein the purification apparatus comprises:
    a column;

a feed inlet, wherein the feed inlet is connected to the column and configured to allow a feed stream comprising 5-(halomethyl)furfural to enter into the column;

a vapor outlet, wherein the vapor outlet is connected to the column and configured to allow gaseous 5-(halomethyl)furfural produced to exit the column;

a bottoms outlet, wherein the bottoms outlet is connected to the column and configured to allow bottoms remaining from the feed stream to exit the column; and a heat source, wherein the heat source is configured to heat the column.

19. The system of any one of embodiments 14 to 17, wherein the purification apparatus comprises:

a column;

an inlet/outlet; wherein the inlet/outlet is connected to the column and configured to allow a feed stream comprising 5-(halomethyl)furfural to enter into the column and to allow gaseous 5-(halomethyl)furfural produced to exit the column; and a heat source, wherein the heat source is configured to heat the column.

20. The system of any one of embodiments 14 to 17, wherein the purification apparatus comprises:

a still flask, wherein the still flask is configured to receive a feed stream comprising 5-(halomethyl)furfural;

a receiving flask, wherein the receiving flask is configured to receive gaseous 5-(halomethyl)furfural produced from the feed stream in the still flask, and wherein the receiving flask is connected to the still flask;

a heat source, wherein the heat source is configured to heat the still flask; and a cooling source, wherein the cooling source is configured to cool the receiving flask.

EXAMPLES

The following Examples are merely illustrative and are not meant to limit any aspects of the present disclosure in any way.

Example 1

Distillation to Purify 5-(Chloromethyl)Furfural (CMF) Using Toluene

Crude CMF and toluene were combined and washed with brine (2×100 mL, 20° C.; saturated aqueous solution of sodium chloride) in a separatory funnel in order to remove trace amounts of hydrochloric acid and water. The oven on a kugelrohr apparatus was pre-heated to 110° C. The bottoms flask of the kugelrohr apparatus was charged with 86.5 g of the washed solution containing the crude CMF and toluene were loaded into the oven. In turn, the receiving flask was chilled to 0° C., and the system was evacuated to about 90 torr. The distillation of toluene was continued until no visible material was observed to be distilling from the bottoms flask (about 1 hr). The kugelrohr apparatus was allowed to return to atmospheric pressure. In turn, the receiving flask containing the toluene was replaced with a clean distillate flask. The system was evacuated to about 90 torr, the oven temperature was raised to 190° C., and the distillate flask was chilled to 0° C. Under these conditions, CMF distilled into the distillate bulb (6.01 g collected), indicating that there was an undetectable amount of impurities in the CMF collected. The run time was for 1 hour and 45 min to remove all of the CMF from the bottoms. Distillation yield was not determined, and samples were not taken after the brine wash for analysis.

Analytical Methods

CMF was analyzed according to the following protocol. Quantitation of CMF by HPLC was performed on an Agilent 1100 HPLC with UV detection at 280 nm. The column was an Agilent RX-Sil, 4.6×100 mm column with 1.8 um particle size. The mobile phase was 4:1 hexane/tetrahydrofuran pumped at 1 mL/min at a temperature of 50° C. A 1 uL injection was used. The retention time for CMF was typically observed around 2.7 minutes. CMF was quantitated by comparison of peak areas to a known standard concentration of CMF.

Example 2

Distillation to Purify 5-(Chloromethyl)Furfural (CMF) Using Linear Alkyl Benzenes The oven on a kugelrohr apparatus was pre-heated to 190° C. The bottoms flask was charged with a crude CMF, toluene and a linear alkyl benzene (run #1: Cepsa Petrelab 550-Q; run #2: Cepsa Petrene 900-Q). The amounts of crude CMF, toluene and linear alkyl benzene for each reaction are summarized in Table 1 below. In turn, the receiving flask was chilled to 0° C., and the kugelrohr apparatus was evacuated to about 90 torr. Under these conditions, CMF distilled into the distillate bulb. An undetectable amount of impurities in the CMF collected. CMF was analyzed according to the following protocol described in Example 1 above.

TABLE 1

| Run # | Mass of Crude CMF and Toluene (g) | linear alkyl benzene | Mass of linear alkyl benzene (g) | Mass of Distillate Collected (g) | Mass of CMF in Distillate (g) |
|---|---|---|---|---|---|
| 1 | 115.5 | Cepsa Petrelab 550-Q | 157 | 68 | 44.9 |
| 2 | 127 | Cepsa Petrene 900-Q | 181 | 88.5 | 83.1 |

Example 3

Distillation of Crude 5-(Chloromethyl)Furfural (CMF) without Solvent

To the bottom flask of the kugelrohr apparatus was added 6.35 g of crude CMF (composed of 5.2 g of CMF, 82% pure). The system was evacuated to about 20 torr and then the receiving flask was chilled to −78° C. The CMF started to distill at 151° C. The temperature was ramped up slowly up to 160° C. to distill more CMF. Total duration: 3 hours. The distillation yielded 3.23 g of CMF (102% pure), and 0.2 g of CMF was recovered in the bottom flask which gives a mass recovery of 66% in CMF.

Distillation yield and mass recovery were calculated as follows:

Distillation yield=(mass of CMF in distillate flask at the end of the process/mass of CMF in still flask at the beginning of the process)×100%

Mass recovery of CMF=([mass of CMF in still flask at the end of the process+mass of CMF in distillate flask at the end of the process]/mass of CMF in still flask at the beginning of the process)×100%

The results are summarized as follows:
Initial CMF purity: 82%
Final CMF purity: 102%
Distillation yield: 62%
Mass recovery of CMF: 66%

Example 4

Distillation of Crude 5-(Chloromethyl)furfural (CMF) in Wibaryl® A

To the still flask of the kugelrohr apparatus was added 39 g of crude CMF (composed of 19.4 g of CMF (49%) and 17.3 g of toluene (39%)), 3.9 g of NaCl and 40.5 g of Wibaryl® A. To remove toluene, 500 ml of organic effluent (5.2 g of CMF, 1% loading) was concentrated under vacuum to give the crude oil CMF used for the distillation.

The CMF loading for the distillation in Wibaryl® A was 25%. The system was evacuated to about 1 torr and then the distillate flask was chilled to −78° C. At first the toluene was distilled at 35-40° C. over 1.5 h. The vacuum and heating was stopped and the toluene was removed. Then the system was again evacuated to about 1 torr and then the new distillate flask was chilled again to −78° C. The CMF started to distill at 80° C. The temperature was ramped up slowly up to 110° C. to distill more CMF. Total duration: 4.5 hours Distillation yield and mass recovery were calculated as set forth in Example 3 above. The results are summarized as follows:
Initial CMF purity: 49%
Final CMF purity: 96.5%
Distillation yield: 80%
Mass recovery of CMF: 81%

Example 5

Argon Stripping of Crude 5-(Chloromethyl)furfural (CMF) in Wibaryl® A

To a two-neck-round-bottom flask (still flask) were added 82.5 g of crude CMF (58.1 g of CMF, 70.5% pure) and 253.5 g of Wibaryl® A (3:1 ratio with crude CMF). One of the necks of the flask was then connected through a distillation adapter to another two-neck-round-bottom flask (distillate flask). The other neck was equipped with a gas dispersion apparatus to ensure homogeneous flow of argon through the solution mixture. The distillate flask was chilled to −90° C. (Liquid $N_2$/Hexane mixture). The remaining neck of the distillate flask was connected through a hose to a cold finger trap cooled at −90° C. (Liquid $N_2$/Hexane mixture). Argon was vigorously bubbled (2 psi) in the flask containing the crude CMF and this solution was also heated gradually from 60° C. to 190° C. for 9 hours to promote more CMF to be stripped and isolated in the distillate flask. The CMF started to distill slowly around 90° C. but more material was trapped around 165° C. The stripping experiment yielded 6.5 g of CMF (97.6% pure) and 6.15 g of CMF was recovered in the still flask which gives a mass recovery of 22%.

The stripping yield and mass recovery were calculated as follows:

Stripping yield=(mass of CMF in distillate flask at the end of the process/mass of CMF in still flask at the beginning of the process)×100%

Mass recovery of CMF=([mass of CMF in still flask at the end of the process+mass of CMF in distillate flask at the end of the process]/g CMF in still flask at the beginning of the process)×100%

The results are summarized as follows:
Initial CMF purity: 70.5%
Final CMF purity: 97.6%
Stripping yield: 11.2%
Mass recovery of CMF: 22%

What is claimed is:

1. A method for purifying 5-(halomethyl)furfural, comprising:
   a) providing a 5-(halomethyl)furfural composition to a purification apparatus, wherein the 5-(halomethyl)furfural composition comprises 5-(halomethyl)furfural and one or more impurities, and wherein the 5-(halomethyl)furfural composition has a mass ratio of the one or more impurities to the 5-(halomethyl)furfural;
   b) providing a solvent to the purification apparatus, wherein the solvent has a boiling point at or above the boiling point of the 5-(halomethyl)furfural;
   c) contacting the 5-(halomethyl)furfural composition and the solvent to form a mixture; and
   d) boiling the mixture to produce a gaseous 5-(halomethyl)furfural, wherein the gaseous 5-(halomethyl)furfural has a mass ratio of the one or more impurities to the 5-(halomethyl)furfural that is lower than the mass ratio for the 5-(halomethyl)furfural composition.

2. The method of claim 1, wherein the solvent comprises one or more alkyl phenyl solvents, one or more heavy alkane solvents, one or more ester solvents, one or more aromatic solvents, one or more silicone oils, or any combinations or mixtures thereof.

3. The method of claim 2, wherein the solvent comprises one or more linear alkyl benzenes.

4. The method of claim 1, wherein the solvent comprises dodecylbenzene, pentylbenzene, hexylbenzene, sulfolane, hexadecane, heptadecane, octadecane, icosane, heneicosane, docosane, tricosane, tetracosane, or any combinations or mixtures thereof.

5. The method of claim 1, further comprising condensing the gaseous 5-(halomethyl)furfural to obtain purified 5-(halomethyl)furfural in liquid form.

6. The method of claim 1, further comprising depositing the gaseous 5-(halomethyl)furfural to obtain purified 5-(halomethyl)furfural in solid form.

7. The method of claim 1, wherein the 5-(halomethyl)furfural is 5-(chloromethyl)furfural.

8. The method of claim 1, further comprising:
   i) providing a stripping agent to the purification apparatus, wherein the stripping agent has a vapor pressure at or above the vapor pressure of 5-(halomethyl)furfural; and
   ii) vaporizing the 5-(halomethyl)furfural in the mixture by contacting the stripping agent with the mixture to form a second gaseous 5-(halomethyl)furfural, wherein the second gaseous 5-(halomethyl)furfural has a mass ratio of the one or more impurities to the 5-(halomethyl)furfural that is lower than the mass ratio for the 5-(halomethyl)furfural composition.

* * * * *